(12) United States Patent
Scott et al.

(10) Patent No.: US 9,546,233 B2
(45) Date of Patent: Jan. 17, 2017

(54) METAL COMPLEX WITH A LEWIS BASE LIGAND

(71) Applicant: LANXESS Elastomers B.V., Geleen (NL)

(72) Inventors: Richard Thomas William Scott, Maastricht (NL); Martin Alexander Zuideveld, Kelmis (BE); Philip Mountford, Oxford (GB)

(73) Assignee: ARLANXEO NETHERLANDS B.V., Geleen (NL)

( * ) Notice: Subject to any disclaimer, the term of this patent is extended or adjusted under 35 U.S.C. 154(b) by 0 days.

(21) Appl. No.: 14/889,596

(22) PCT Filed: May 7, 2014

(86) PCT No.: PCT/EP2014/059354
§ 371 (c)(1),
(2) Date: Nov. 6, 2015

(87) PCT Pub. No.: WO2014/180913
PCT Pub. Date: Nov. 13, 2014

(65) Prior Publication Data
US 2016/0115265 A1    Apr. 28, 2016

(30) Foreign Application Priority Data
May 8, 2013  (EP) ..................... 13167138

(51) Int. Cl.
| C08F 4/6592 | (2006.01) |
| C08F 210/16 | (2006.01) |
| C08F 4/62 | (2006.01) |
| C07F 17/00 | (2006.01) |
| C07F 7/28 | (2006.01) |
| C08F 4/659 | (2006.01) |

(52) U.S. Cl.
CPC ............... *C08F 210/16* (2013.01); *C07F 7/28* (2013.01); *C07F 17/00* (2013.01); *C08F 4/6592* (2013.01); *C08F 4/65908* (2013.01); *C08F 4/65912* (2013.01); *C08F 2420/04* (2013.01)

(58) Field of Classification Search
CPC ........ C07F 17/00; C08F 4/6592; C08F 210/16
See application file for complete search history.

(56) References Cited

U.S. PATENT DOCUMENTS

| 7,732,643 B2 * | 6/2010 | Hanaoka | ................ C07C 33/34 568/308 |
| 7,956,140 B2 | 6/2011 | Ijpeij et al. | |
| 8,957,170 B2 * | 2/2015 | Van Doremaele | .... C08F 210/18 502/103 |
| 2013/0066028 A1 * | 3/2013 | Van Doremaele | .... C08F 210/18 526/170 |

OTHER PUBLICATIONS

Hair, et al., "Insertion and Coordination Reactions of Titanium(IV) Metallocene Zwitterions", Organometallics, 2001, 20(1), pp. 177-181, Abstract, American Chemical Society, Washington, DC, USA, obtained from http://pubs.acs.org/doi/abs/10.1021/0m0002327 on Sep. 16, 2016, two pages.

Yasuda, H. et al., "1,3-Diene Complexes of Zirconium and Hafnium Prepared by the Reaction of Enedlylmagnesium with . ..", Organometallics 1982, 1, American Chemical Society, Washington, DC, USA, pp. 388-396.

Yasuda, Hajime, et al., "Unique Chemical Behavior and Bonding of Early-Transition-Metal-Diene Complexes", Am. Chem. Res. 1985, 18, American Chemical Society, Washington, DC, USA pp. 120-126.

Erker, Gerhard, "The Remarkable Features of (n4—Conjugated Diene) zirconocene and -hafnocene Complexes", Advances in Organometallic Chemistry, vol. 24, 1985, pp. 1-39, Abstract, obtained from http://www.sciencedirect.com/science/article/pii/S0065305508604128?np=y on Sep. 16, 2016, three pages.

Chen, Eugene You-Xian, et al., "Cocatalysts for Metal-Catalyzed Olefibn Polymerization: Activators, Activation Processes, and Structure-Activity RElationships", Chem Rev. 2000, 100, American Chemical Society, Washington, DC. pp. 1391-1434.

Kissounko, Denis A., et al., "Synthesis and characterization of cationic and xwitterionic allyl zirconium complexes derived from . . .", Journal of Organometallic Chemistry, vol. 683, No. 1, 2003, Elsevier Science B.V., Netherlands, pp. 29-38.

International Search Report from International Application No. PCT/EP2014/059354, dated May 30, 2014, one page.

* cited by examiner

*Primary Examiner* — Caixia Lu

(57) ABSTRACT

A metal complex of the formula (1)

$$CyAMX(L)_n \qquad (1)$$

wherein
Cy is a cyclopentadienyl-type ligand,
M is a metal of group 4;
A is an amidine-containing ligand moiety, represented by formula 2:

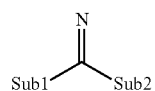

(2)

wherein the amidine-containing ligand is covalently bonded to the metal M via the imine nitrogen atom, and Sub1 is a substituent comprising a group 14 atom through which Sub1 is bonded to the imine carbon atom and Sub2 is a substituent comprising a heteroatom of group 15, through which Sub2 is bonded to the imine carbon atom;
X is an allyl borate ligand derived from a conjugated diene ligand, D, and a borane, B and
L is a neutral Lewis basic ligand wherein the number of said metal ligands "n" is in the range of 1 to the amount that specifies the 18-electron rule.

18 Claims, 1 Drawing Sheet

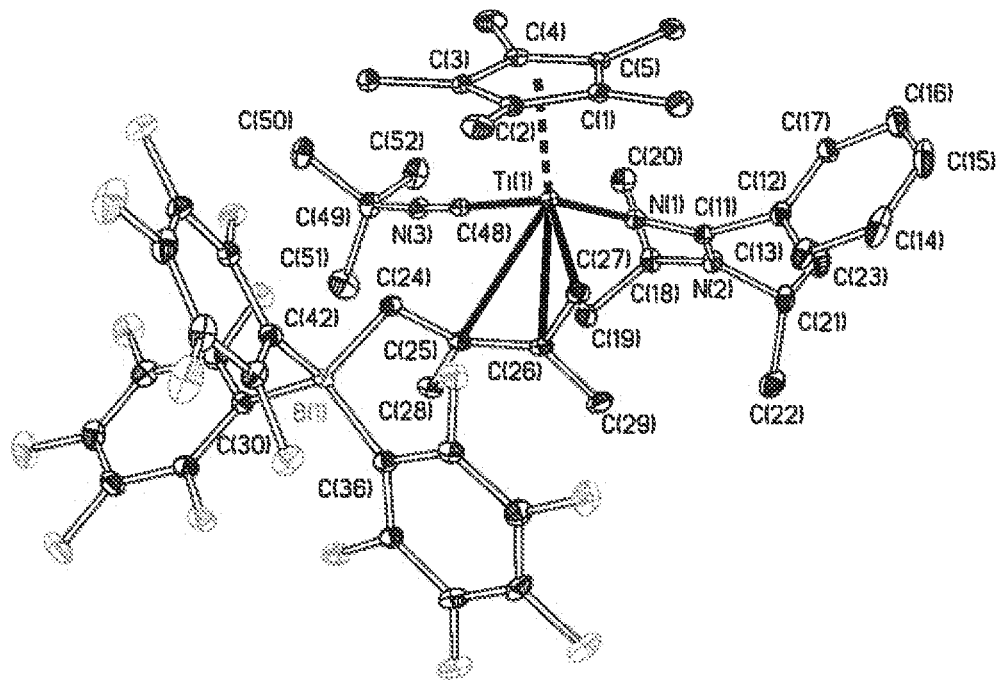
Figure 1 – X-ray picture of compound 3
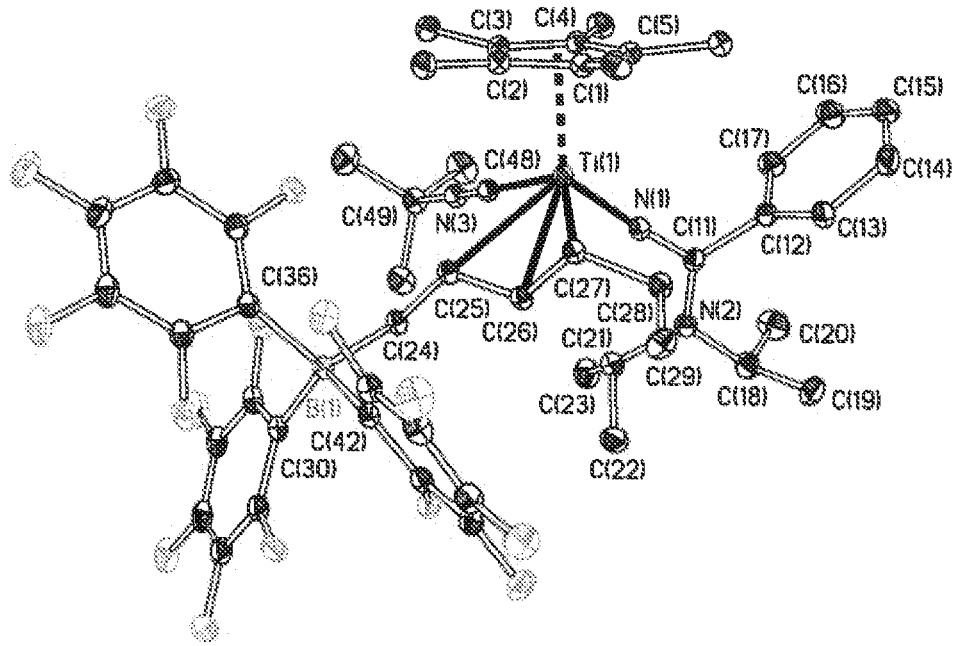
Figure 2 – X-ray picture of compound 4

METAL COMPLEX WITH A LEWIS BASE LIGAND

The present invention relates to a metal complex containing a Lewis base ligand, a process for its preparation, a catalyst system containing said metal complex and a process for manufacturing polymers wherein said metal complex or catalyst system is used.

A process for the polymerization of at least one olefin having 2 to 8 carbon atoms in the presence of a polymerization catalyst component comprising an amidine ligand, an activator, and optionally a scavenger is known from WO2005090418. WO2005090418 which disclose a process for the copolymerization of ethylene and at least one additional alpha olefin having from 3 to 8 carbon atoms. Characterized in that said process employs a catalyst system for olefin polymerization comprising: an organometallic complex of a group 4 metal comprising an amidine ligand; and an activator. WO2005090418 discloses also a process for the copolymerisation of ethylene, alpha olefin and one or more non conjugated dienes. Borate, borane or highly reactive alkylaluminoxanes are required for efficient activation of the organometallic complex.

A catalyst component comprising cyclopentadienyl, amidine and diene ligands is known from WO2011076772 and WO2011076775. Such catalyst components when employed with a co-catalyst is known to afford a catalyst system which displays capability to polymerize higher alpha-olefins with ethylene and optionally one or more non-conjugated diene. It is known that distinct disadvantages of such catalyst components is the necessity to dose to the reactor a co-catalyst such as a borate, borane or a highly reactive alkylaluminoxanes component in order for efficient activation.

The object of the present invention was to provide a catalyst component which may be more efficiently activated. Furthermore, such efficient activation of the catalyst component may be achieved by and less reactive co-catalysts. This also makes for a less complex catalyst system which may comprise fewer components.

This objective is achieved with a metal complex of the formula (1)

  (1)

wherein
Cy is a cyclopentadienyl-type ligand,
M is a metal of group 4;
A is an amidine containing ligand moiety, represented by formula 2:

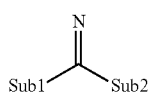  (2)

wherein the amidine-containing ligand is covalently bonded to the metal M via the imine nitrogen atom, and Sub1 is a substituent comprising a group 14 atom through which Sub1 is bonded to the imine carbon atom and Sub2 is a substituent comprising a heteroatom of group 15, through which Sub2 is bonded to the imine carbon atom;
X is an allyl borate ligand derived from a conjugated diene ligand, D, and a borane, and
L is a neutral Lewis basic ligand wherein the number of said metal ligands "n" is in the range of 1 to the amount that satisfies the 18 electron rule.

Although certain Lewis base ligand containing metal complexes are known from Cowley at al., Organometallics, 20, 177 (2001), they were only made in order to study the coordination of donors ligands to zwitterionic complexes by spectroscopic techniques and X-ray crystallography.

M

In a preferred embodiment the metal M of group 4 is titanium (Ti), zirconium (Zr) or hafnium (Hf), most preferably titanium.

Cy

A preferred cyclopentadienyl-type ligand is mono or polysubstituted wherein the substituents are selected from the group consisting of halogen, substituted or unsubstituted hydrocarbyl, substituted or unsubstituted hydrocarbyloxy, substituted or unsubstituted silyl and substituted or unsubstituted germyl residues as well as amido and phosphide radicals. Possible substituents are halogen, amido, phosphide, alkoxy, or aryloxy residues. As used herein, the term substituted cyclopentadienyl-type ligand is meant to broadly convey its conventional meaning, namely a substituted ligand having a five-membered carbon ring which is bonded to the metal via a Tr-type bonding usually in adopting $\eta^5$-coordination to the metal.

Thus, the term cyclopentadienyl-type includes cyclopentadienyl, indenyl and fluorenyl. The term mono- or polysubstituted refers to the fact that one or more aromatic hydrogen atoms of the cyclopentadienyl-type structure have been replaced by one or more other residues. The number of substituents is between 1 and 5 for the cyclopentadienyl ligand, 1 to 7 for the indenyl ligand and 1 to 9 for the fluorenyl ligand.

An exemplary list of substituents for a cyclopentadienyl ligand includes the following groups. For halogen F, Cl and Br may be mentioned.

For substituted or unsubstituted hydrocarbyl radicals are preferred including $C_1$-$C_{20}$ linear and branched alkyl radicals such as methyl, ethyl, propyl, butyl, pentyl, hexyl, heptyl, octyl, nonyl, and decyl, $C_1$-$C_{20}$ hydrocarbyl-substituted and unsubstituted cyclic aliphatic and polycyclic aliphatic radicals such as cyclopropyl, cyclobutyl, cyclopentyl, cyclohexyl, phenylcyclohexyl, methylcyclohexyl, cycloheptyl, cyclooctyl, cyclodecyl, cyclododecyl, isopropyldodecyl, adamantyl, norbornyl, tricyclo[5.2.1.0]decyl; $C_1$-$C_{20}$ hydrocarbyl-substituted and unsubstituted aryl radicals including phenyl, methylphenyl, trimethylphenyl, cyclohexylphenyl, napthyl, butylphenyl, butyldimethylphenyl; C1-20 substituted hydrocarbyl radicals including benzyl, N,N-dimethylaminobenzyl, N,N-dimethylaminomethyl, methoxymethyl, diphenylphosphinomethyl, fluorophenyl, trifluoromethylphenyl, fluoromethyl and cyanoethyl.

The preferred substituted or unsubstituted silyl and substituted or unsubstituted germyl residues include Si—$(R^6)_3$ wherein each $R^6$ is selected from the group consisting of hydrogen, $C_{1-8}$ alkyl or alkoxy radical, $C_{6-10}$ aryl or aryloxy, in particular tris(trifluoromethyl)silyl or tris(perfluorophenyl)silyl, and germyl radicals of the formula —Ge—$(R^7)_3$ wherein each $R^7$ is selected from the group consisting of hydrogen, $C_{1-8}$ alkyl or alkoxy radical, $C_{6-10}$ aryl or aryloxy radical like tris(trifluoromethyl)germyl, or tris(perfluorophenyl)germyl.

The preferred substituted or unsubstituted hydrocarbyloxy radicals include methoxy, ethoxy, butoxy, phenoxy, methylthio, ethylthio and phenylthio.

The preferred amido and phosphido radicals include an amido which is unsubstituted or substituted by up to two $C_{1-8}$ alkyl radicals, and a phosphido radical which is unsubstituted or substituted by up to two $C_{1-8}$ alkyl radicals.

In a preferred embodiment the cyclopentadienyl ligand is penta substituted by methyl groups and in consequence Cy is 1,2,3,4,5-pentamethyl-cyclopentadienyl, $C_5Me_5$, commonly referred to as Cp*. Also preferred Uganda Cy are other unsubstituted or substituted cyclopentadienyl groups, substituted or unsubstituted indenyl groups, substituted or unsubstituted fluorenyl groups, substituted or unsubstituted tetrahydroindenyl groups, substituted or unsubstituted tetrahydrofluorenyl groups, substituted or unsubstituted octahydrofluorenyl groups, substituted or unsubstituted benzoindenyl groups, substituted or unsubstituted heterocyclopentadienyl groups, substituted or unsubstituted heteroindenyl groups, substituted or unsubstituted heterofluorenyl groups, or their isomers.

A

A preferred embodiment of the invention relates to the metal complex of the formula (1) containing an amidine-containing ligand A of formula (2) wherein Sub1 is an aryl residue. Typical examples for such a preferred amidinate-containing ligand are represented by formula 2 with Sub1 being a phenyl or substituted phenyl residue, preferable naphthyl, 2,6-dimethyl phenyl, 2,6-dichlorophenyl or 2,6-difluorophenyl.

A further embodiment of the invention relates to a metal complex of formula (1) wherein Sub1 is an alkyl residue. Typical examples for such a preferred Sub1 are linear, branched or cyclic alkyl residue with 1 to 20 carbon atoms, unsubstituted or substituted with halogen, amide, silyl or aryl radicals. Examples for such Sub1 are methyl, hexyl, cyclohexyl, isopropyl, tert-butyl, benzyl, trifluoromethyl, 2,6-dimethyl benzyl, 2,6-difluoro benzyl and 2,6-difluorophenyl.

Another preferred embodiment of the present invention relates to a metal complex of the formula (1) wherein Sub2 is of the general formula —$NR^4R^5$ with $R^4$ and $R^5$ being individually selected from the group of aliphatic hydrocarbyl, halogenated aliphatic hydrocarbyl, aromatic hydrocarbyl and halogenated aromatic hydrocarbonyl residues. $R^4$ optionally forming a heterocyclic structure with $R^5$ or Sub1. Examples for Sub2 are dimethylamide, diisopropylamide, biscyclohexyl amide, and N-dimethylphenyl N-ethyl amide. Most preferred examples of the amidinate-containing ligand represented by the formula (1) are based on amidines of the formula (2a)

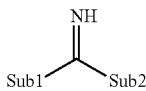

(2a)

Examples include N,N-dimethylacetimidamide, N,N-diisopropylacetimidamide, N,N-dicyclohexylacetimidamide, N-(2,6-dimethylphenyl)-N-ethylacetimidamide, N,N-dimethylisobutyrimidamide, N,N-dlisopropylisobutyrimidamide, N,N-dicyclohexylisobutyrimidamide, N-(2,6-dimethylphenyl)-N-ethylisobutyrimidamide, N,N-dimethylcyclohexanecarboximidamide, N,N-diisopropylcyclohexanecarboximidamide, N,N-dicyclohexylcyclohexanecarboximidamide, N-(2,6-dimethylphenyl)-N-ethylcyclohexanecarboximidamide, N,N-dimethylpivalimidamide, N,N-diisopropylpivalimidamide, N,N-dicyclohexylpivalimidamide, N-(2,6-dimethylphenyl)-N-ethylpivalimidamide, 2,2,2-trifluoro-N,N-dimethylacetimidamide, 2,2,2-trifluoro-N,N-diisopropyfacetimidamide, N,N-dicyclohexyl-2,2,2-trifluoroacetimidamide, N-(2,6-dimethylphenyl)-N-ethyl-2,2,2-trifluoroacetimidamide, 2-(phenyl)-N,N-dimethylacetimidamide, 2-(phenyl)-N,N-diisopropylacetimidamide, N,N-dicyclohexyl-2-(phenyl)acetimidamide, 2-(phenyl)-N-(2,6-dimethylphenyl)-N-ethylacetimidamide, 2-(2,6-dimethylphenyl)-N,N-dimethylacetimidamide, 2-(2,6-dimethylphenyl)-N,N-diisopropylacetimidamide, N,N-dicyclohexyl-2-(2,6-dimethylphenyl)acetimidamide, N,2-bis(2,6-dimethylphenyl)-N-ethylacetimidamide, 2-(2,6-difluorophenyl)-N,N-dimethylacetimidamide, 2-(2,6-difluorophenyl)-N,N-diisopropylacetimidamide, N,N-dicyclohexyl-2-(2,6-difluorophenyl)acetimidamide, 2-(2,6-difluorophenyl)-N-(2,6-dimethylphenyl)-N-ethylacetimidamide, N,N-dimethylbenzimidamide, N,N-diisopropyibenzimidamide, N,N-dicyclohexylbenzimidamide, N-(2,6-dimethylphenyl)-N-ethylbenzimidamide, N,N-dimethyl-1-naphthimidamide, N,N-diisopropyl-1-naphthimidamide, N,N-dicyclohexyl-1-naphthimidamide, N-(2,6-dimethylphenyl)-N-ethyl-1-naphthimidamide, N,N,2,6-tetramethylbenzimidamide, N,N-diisopropyl-2,6-dimethylbenzimidamide, N,N-dicyclohexyl-2,6-dimethylbenzimidamide, N-(2,6-dimethylphenyl)-N-ethyl-2,6-dimethylbenzimidamide, 2,6-difluoro-N,N-dimethylbenzimidamide, 2,6-difluoro-N,N-diisopropyibenzimidamide, N,N-dicyclohexyl-2,6-difluorobenzimidamide, N-(2,6-dimethylphenyl)-N-ethyl-2,6-difluorobenzimidamide, 2,6-dichloro-N,N-dimethylbenzimidamide, 2,6-dichloro-N,N-diisopropylbenzimidamide, 2,6-dichloro-N,N-dicyclohexylbenzimidamide, 2,6-dichloro-N-(2,6-dimethylphenyl)-N-ethylbenzimidamide. Preferred examples are 2,6-difluoro-N,N-diisopropylbenzimidamide and N,N-diisopropylbenzimidamide.

L

Preferred is a metal complex of the formula (1) wherein L is an ether, a thioether, a amine, a tertiary phosphane, an imine, a nitrile, an isonitrile, or a bi- or oligodentate donor.

If more than one ligand L is present they may have different meanings.

The number "n" of neutral ligands in the metal complex of formula (1) may range from 1 to the amount that satisfies the 18 electron rue, as known in the art. Preferably from 1 to 2. In the preferred embodiment the number of neutral ligands is 1.

Suitable ethers are diethyl ether, dipropyl ether, diisopropyl ether, dibutyl ether, dihexyl ether, anisole, phenetole, butyl phenyl ether, methoxytoluene, benzyl ethyl ether, diphenyl ether, dibenzyl ether, veratrole, 2-epoxypropane, dioxane, trioxane, furan, 2,5-dimethylfuran, tetrahydrofuran, tetrahydropyrane, 1,2-diethoxyethane, 1,2-dibutoxyethane, and crown ethers. Suitable thioethers are dimethyl sulfide, diethyl sulfide, thiophene, and tetrahydrothiophene. Suitable amines such as methylamine, dimethylamine, trimethylamine, ethylamine, diethylamine, triethylamine, propylamine, diisopropylamine, butylamine, isobutylamine, dibutylamine, tributylamine, pentylamine, dipentylamine, tripentylamine, 2-ethylhexylamine, allylamine, aniline, N-methylaniline, N,N-dimethylaniline, N,N-diethylaniline, toluidine, cyclohexylamine, dicyclohexylamine, pyrrole, piperidine, pyridine, picoline, 2,4-lutidine, 2,6-di(t-butyl) pyridine, quinoline, and isoquinoline, preferably tertiary amines such as trialkylamines, pyridine, bipyridine, tetramethylethylenediamine (TMEDA), and (−)-sparteine). Suitable tertiary phosphanes are triphenylphoshine and trialkylphosphanes. Suitable of imines are ketimines, guanidines, iminoimidazolidines, phosphinimines and amidines. Suitable bidentate ligands are diimines, alkyl or aryldiphoshanes, dimethoxyethane. Suitable oligodentate ligands are triimines (such as tris(pyrazolyl)alkanes), cyclic multidentate ligands comprising heteroatoms of group 13-17, including crown ethers optionally having heteroatoms of group 13-17, azo-crown ethers optionally having heteroatoms of group 13-17, phospha-crown ethers optionally having heteroatoms of group 13-17, crown ethers having combinations of heteroatoms of group 15-16 optionally having heteroatoms of group 13-17 and crown ethers containing heteroatoms of group 14-17 or combinations thereof.

Suitable nitriles are those of the formula, $R^1C\equiv N$, where is individually selected from the group of aliphatic hydrocarbyl, halogenated aliphatic hydrocarbyl, aromatic hydrocarbyl and halogenated aromatic hydrocarbonyl residues. Preferred nitriles are acetonitrile, acrylonitrile, cyclohexanedintirile, benzonitrile, pentafluorbenzonitrile, 2,6-difluorobenzonitrile, 2,6-dichlorobenzonitrile, 2,6-dibromobenzonitrile, 4-fluoro-2-trifluoromethyl benzonitrile, 3-pyridinecarbonitrile Suitable isonitriles are those of the formula, $R^2N\equiv C$, where $R^1$ is individually selected from the group of aliphatic hydrocarbyl, halogenated aliphatic hydrocarbyl, aromatic hydrocarbyl and halogenated aromatic hydrocarbonyl residues. Preferred isonitriles are ten-butyl isocyanide ($^tBuNC$), ethyl isocyanoacetate, p-toluenesulfonylmethyl isocyanide and cyclohexyl isocyanide preferably tert-butyl isonitrile ($^tBuNC$).

A preferred neutral Lewis basic ligand L means t-Butylisonitrile ($^tBuNC$).

X

A preferred ligand X is an allyl borate ligand.

Preferably X is derived from a reaction of an organometallic precursor comprising a conjugated diene ligand, D, with a borane, B. Conjugated diene ligands t may be associated with the metal in either an s-trans configuration (π-bound) or in an s-cis configuration (either π-bonded or σ-bonded). In the metal complexes used as precursors for forming the X ligand a diene ligand group, D, is preferably π-bound. Such a bonding type is readily determined by X-ray crystallography or by NMR spectral characterization according to the techniques of Yasuda, et al., Organometallics, 1, 388 (1982), Yasuda, et al., Acc. Chem. Res., 18, 120 (1985), and Erker, et al., Adv. Organomat. Chem., 24, 1 (1985), as well as the references cited therein. By the term "π-complex" is meant both the donation and back acceptance of electron density by the ligand which is accomplished using ligand π-orbitals. Preferably the complexes do contain a ligand D that does not comprise a cyclopentadienyl group, preferably also no anionic and no aromatic π-bonded group. Preferably X is derived from conjugated diene ligand which is a $C_4$-$C_{40}$ diene, wherein the conjugated diene, is a $C_4$-$C_{40}$ diene optionally substituted with one or more groups independently selected from the group consisting of hydrocarbyl, silyl, and halogenated carbyl. Examples of suitable conjugated dienes D include: butadiene, isoprene, 1,3-pentadiene, 1,4-diphenyl-1,3-butadiene 2,3-diphenyl-1,3-butadiene, 1-methyl-1,3-pentadiene; 1,4-dibenzyl-1,3-butadiene; 2,4-hexadiene; 2,4,5,7-tetramethyl-3,5-octadiene; 2,2,7,7-tetramethyl-3,5-octadiene; 1,4-ditolyl-1,3-butadiene, 1,4-bis(trimethylsilyl)-1,3-butadiene; 2,3-dimethyl-1,3-butadiene and 1,4-dimethyl-1,3-butadiene. Preferred is a methyl or phenyl mono or disubstituted 1,3-butadiene, in particular 1,4-diphenyl-1,3-butadiene, 2,3-diphenyl-1,3-butadiene, 2,3-dimethyl-1,3-butadiene and 1,4-dimethyl-1,3-butadiene.

The borane, B may be any of a boron compound (B1) represented by the general formula $BQ_1Q_2Q_3$.

In the boron compound (B1) represented by the general formula $BQ_1Q_2Q_3$, B is a boron atom in the trivalent valence state, $Q_1$ to $Q_a$ are a halogen atom, hydrocarbon group, halogenated hydrocarbon group, substituted silyl group, alkoxy group or di-substituted amino group, and they may be the same or different. $Q_1$ to $Q_3$ are preferably a halogen atom, hydrocarbon group having 1 to 20 carbon atoms, halogenated hydrocarbon group having 1 to 20 carbon atoms, substituted silyl group having 1 to 20 carbon atoms, alkoxy group having 1 to 20 carbon atoms or amino group having 2 to 20 carbon atoms, and more preferably, $Q_1$ to $Q_3$ are a halogen atom, hydrocarbon group having 1 to 20 carbon atoms, or halogenated hydrocarbon group having 1 to 20 carbon atoms. Further preferably, $Q_1$ to $Q_3$ are a fluorinated hydrocarbon group having 1 to 20 carbon atoms containing at least one fluorine atom, and particularly preferably, $Q_1$ to $Q_3$ are a fluorinated aryl group having 6 to 20 carbon atoms containing at least one fluorine atom. Specific examples of the compound (B1) include tris(pentafluorophenyl)borane, tris(2,3,5,6-tetrafluorophenyl)borane, tris(2,3,4,5-tetrafluorophenyl)borane, tris(3,4,5-trifluorophenyl) borane, tris(2,3,4-trifluoro-phenyl)-borane, phenylbis(pentafluorophanyl)borane and the like and tris(pentafluorophenyl)borane ($B(C_6F_5)_3$) is most preferable.

Preferred metal complexes of formula (1) are those, wherein

M means Ti,

Cy means pentamethylcyclopentadienyl

A means an amidine radical of formula (2) wherein

Sub1 means an unsubstituted or substituted phenyl, whereas substituents halogen, in particular Cl or F and $C_1$-$C_4$-alkyl, in particular methyl are preferred and Sub2 means $—NR^4R^5$ wherein $R^4$ and $R^5$ have the meaning given above, X means an allyl borate derived from unsubstituted or substituted 1,3-butadiene, in particular 1,4-diphenyl-1,3-butadiene, 2,3-diphenyl-1,3-butadiene, 2,3-dimethyl-1,3-butadiene and 1,4-dimethyl-1,3-butadiene and a borate of the formula $BQ_1Q_2Q_3$ wherein $Q^1$-$Q^3$ has the meaning as given above, preferably tris(pentafluoro-phenyl)borane ($B(C_6F_5)_3$) and L means tert-butylisonitrile and n means 1.

One preferred metal complex of the formula (1) has the following formula:

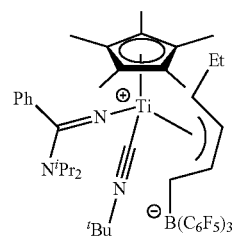

Process

The invention further relates to a process for the manufacturing of a metal complex according to the present invention wherein a metal complex of the formula (3)

CyAMX (3)

is reacted with a Lewis base L wherein the radicals Cy, A, M, X and L have the above given meanings.

Preferably the metal complex of formula (3) is obtained by the reaction of a metal complex of formula (4)

wherein Cy, A and M have the same meanings as in claim 8 and D means a conjugated diene, preferably as mentioned above and a borane.

The reaction of the complex of the formula (4) with the borane, wherein the borane preferably has the meaning of B given above, is done in a suitable solvent at ambient pressure, preferably at 0.9 bar to 1.1 bar and a temperature in the range of −80 to 80° C. More preferably, in the range 0 to 30° C. The molar ratio of formula (4) to borane is preferably in the range of 0.8 to 1.5, most preferably the ratio is 0.95 to 1.050. The reaction is preferably run in the absence of moisture. The zwitterionic complex (3) is usually immediately afforded. Preferably, the reaction is carried out under an atmosphere of a dry, inert gas such as nitrogen. Suitable solvents include aliphatic and aromatic hydrocarbon solvents. Complex (3) may be isolated using techniques well known to those skilled in the art by removal of volatiles under reduced pressure or by crystallisation with subsequent removal of the mother liquor by filtration.

The diene ligand D in the metal complex of the formula (4) may be represented in a π-bound or σ-bound form as shown in formula (1a).

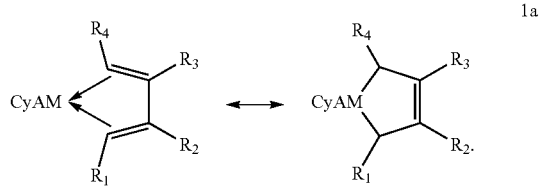

In formula (1a) the radicals R1 to R4 together with the carbon atoms they are bonded to preferably correspond with the definition of the radicals D.

The metal complex (1) can be preferably prepared by reaction of complex 3 with a Lewis base, L, especially tert-butylisonitrile, in a suitable solvent in the absence of moisture. Suitable solvents include aliphatic and aromatic hydrocarbon solvents. Preferably, the reaction is carried out under an atmosphere of a dry, inert gas such as nitrogen. The molar ratio of complex (3) and the Lewis base, L is preferably in the range of 0.8 to 1.5, preferably the ratio is 0.95 to 1.05.

Complex (1) may be isolated using techniques well known to those skilled in the art by removal of volatiles under reduced pressure or by crystallisation with subsequent removal of the mother liquor by filtration.

The invention further provides a catalyst system comprising
a) a metal complex of the formula (1) according to the present invention
and
b) a scavenger.

The preferred metal complex of compound a) is mentioned above. A scavenger is a compound that reacts with impurities present in the process of the invention, which are poisonous to the catalyst.

In a preferred embodiment of the present invention the scavenger b) as of the catalyst system is a hydrocarbyl of a metal or metalloid of group 1-13 or its reaction products with at least one sterically hindered compound containing a group 15 or 16 atom.

Preferably, the group 15 or 1$ atom of the sterically hindered compound bears a proton. Examples of these sterically hindered compounds are tert-butanol, iso-propanol, triphenylcarbinol, 2,6-di-tert-butylphenol, 4-methyl-2,6-di-tert-butylphenol, 4-ethyl-2,6-di-tert-butylphenol, 4-methyl-2,6-di-tert-butylanilin, 4-ethyl-2,6-di-tert-butylanilin, HMDS (hexamethyldisilazane), diisopropylamine, di-tert-butylamine, diphenylamine and the like. Some non-limiting examples of scavengers are butyllithium including its isomers, dihydrocarbylmagnesium, and hydrocarbylzinc and their reaction products with a sterically hindered compound or an acid, such as HF, HCl, HBr, HI. Furthermore organoaluminium compounds (E) as defined below can be used as Scavenger b), in particular hydrocarbylaluminoxanes like isobutylaluminoxane (IBM)).

The catalyst system of the present invention may in addition contain an activator which differs from the used scavenger.

Activators for single-site catalysts are fairly well known in the art. These activators often comprise a group 13 atom, such as boron or aluminium. Examples of these activators are described in *Chem. Rev.*, 2000, 100, 1391 by E. Y-X. Chen and T. J. Marks. A preferred activator is a borane (C1), a borate (C2, C3) or an organoaluminum compound (E) like alkylaluminoxane such as methyl aluminoxane (MAO). The co-catalyst for activation preferably is any boron compound of the following (C1) to (C3) and/or an organoaluminum compound (E). The organoaluminum compound (E) may be employed as a scavenger and/or a co-catalyst.

(C1) A boron compound represented by the general formula $BQ_1Q_2Q_3$ (C2) A boron compound represented by the general formula $G(BQ_1Q_2Q_3Q_4)$ (C3) A boron compound represented by the general formula $(J-H)(BQ_1Q_2Q_3Q_4)$ (wherein, B is a boron atom in the trivalent valence state, $Q_1$ to $Q_3$ have the same meaning as already mentioned above and $Q_4$ has the same meaning as one of the radicals $Q_1$ to $Q_3$ and $Q_1$ to $Q_4$ may be the same or different. G is an inorganic or organic cation, J is a neutral Lewis base, and (J-H) is a Brönsted acid.

In the boron compound (C1) represented by the general formula $BQ_1Q_2Q_3$, B is a boron atom in the trivalent valence state, $Q_1$ to $Q_3$ have the above mentioned meanings and may be the same or different.

Specific examples of the compound (C1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenyl-bis(pentafluoro phenyl)borane and the like, and tris(pentafluorophenyl)borane is most preferable.

In the boron compound (02) represented by the general formula $G(BQ_1Q_2Q_3Q_4)$, $G^+$ is an inorganic or organic cation, B is a boron atom in the trivalent valence state, and $Q_1$ to $Q_4$ are as defined for $Q_1$ to $Q_3$ in the above-mentioned (C1).

Specific examples of the inorganic cation Gin a compound represented by the general formula $G(BQ_1Q_2Q_3Q_4)$ include a ferrocenium cation, alkyl-substituted ferrocenium cation, saver cation and the like, specific examples of the organic cation G thereof include a triphenylmethyl cation and the like. G is preferably a carbenium cation, and particularly preferably a triphenylmethyl cation.

Examples of $(BQ_1Q_2Q_3Q_4)$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluoro-phenyl)borate, tetrakis(3,5-bistrifluoromethylphenyl)borate and the like.

As specific combination of them, ferroceniumtetrakis(pentafluorophenyl)borate, 1,1'-dimethylferroceniumtetrakis(pentafluorophenyl)borate, silvertetrakis(pentafluorophenyl)borate, triphenyimethyltetrakis-(pentafluorophenyl)borate, triphenylmethyl-tetrakis(3,5-bistrifluoromethylphenyl)borate and the like are listed, and triphenyl-methyltetrakis(pentafluorophenyl)borate is most preferable.

In the boron compound (C3) represented by the general formula $(J-H)^+(BQ_1Q_2Q_3Q_4)$, J is a neutral Lewis base, (J-H) is a Bronsted acid, B is a boron atom in the trivalent valence state, and $Q_1$ to $Q_4$ are as defined for $Q_1$ to $Q_4$ in the above-mentioned Lewis acid (C1).

Specific examples of the Bronsted acid $(J-H)^+$ in a compound represented by the general formula (J-H) $(BQ_1Q_2Q_3Q_4)$ include a trialkyl-substituted ammonium, N,N-dialkylanilinium, dialkylammonium, triaryl phosphonium and the like, and as the $(BQ_1Q_2Q_3Q_4)$, the same compounds as described above are listed. As specific combination of them, there are listed triethylammoniumtetrakis(pentafluoro-phenyl)-borate, tripropylammoniumtetrakis(pentafluorophenyl)borate, tri(n-butyl)ammonium-tetrakis(pentafluorophenyl)borate, tri(n-butyl)ammoniumtetrakis(3,5-bistrifluoromethyl-phenyl)borate, N,N-dimethylaniliniumtetrakis(pentafluoro-phenyl)borate, N,N-diethylaniliniumtetrakis(penta-fluorophenyl)borate, N,N-2,4,6-pentamethylanilinium-tetrakis-(pentafluorophenyl)borate, N,N-dimethylanilinium-tetrakis(3,5-bistrifluoromethyl-phenyl)borate, diisopropyl-ammoniumtetrakis(penta-fluorophenyl)borate, dicyclohexyl-ammoniumtetrakis-(pentafluorophenyl)borate, triphenylphosphoniumtetrakis(pentafluorophenyl)borate, tri(methylphenyl)phosphoniumtetrakis(pentafluorophenyl)borate, tri(dimethylphenyl)-phosphonium-tetrakis(pentafluorophenyl)borate and the like, and tri(n-butyl)ammonium-tetrakis(pentafluorophenyl)borate or N,N-dimethylaniliniumtetrakis(pentafluoro-phenyl)borate is most preferable.

The molar ratio of metal complex:activating cocatalyst C1-C3 employed preferably ranges from 1:10 to 1:0, more preferably ranges from 1:5 to 1:0, and most preferably from 1:1 to 1:0.

The organoaluminum compound (E) is an aluminum compound having a carbon-aluminum bond, and one or more of aluminum compounds selected from the following (E1) to (E3) are preferable.

(E1)) organoaluminum compound represented by the general formula $T^1_aAlZ_{3-a}$ (E2) A cyclic aluminoxane having a structure represented by the general formula $\{-Al(T^2)-O-\}_b$ (E3) Linear aluminoxane having a structure represented by the general formula $T^3\{-Al(T^3)-O-\}_cAlT^3_2$ (wherein, each of $T^1$, $T^2$ and $T^3$ is hydrocarbon group, and all $T^1$, all $T^2$ and all $T^3$ may be the same or different respectively. Z represents a hydrogen atom or halogen atom, and all Z's may be the same or different. 'a' represents a number satisfying $0<a\leq3$, 'b' is an integer of 2 or more, and 'c' Is an integer of 1 or more).

The hydrocarbon group in E1, E2 or E3 is preferably a hydrocarbon group having 1 to 8 carbon atoms, and more preferably an alkyl group.

Specific examples of the organoaluminum compound (E1) represented by the general formula $T^1_aAlZ_{3-a}$ include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like; and so forth.

The trialkylaluminum is preferable, and triethylaluminum or triisobutylaluminum is more preferable.

Specific examples of cyclic aluminoxane E2 having a structure represented by the general formula $\{-Al(T^2)-O-\}_b$ and the linear aluminoxane E3 having a structure represented by the general formula $T^3\{-Al(T^3)-O-\}_cAlT^3_2$ include alkyl groups such as a methyl group, ethyl group, n-propyl group, isopropyl group, n-butyl group, isobutyl group, n-pentyl group, neopentyl group and the like, b is an integer of 2 or more, c is an integer of 1 or more. Preferably, $T^2$ and T represent a methyl group or isobutyl group, and b is 2 to 40 and c is 1 to 40. Most preferably, $T^2$ and $T^3$ represent an isobutyl group and b is 2 to 40 and c is 1 to 40.

The above-described aluminoxane is made by various methods. This method is not particularly restricted, and the aluminoxane may be produced according to a known method. For example, a solution prepared by dissolving a trialkylaluminum (for example, trimethylaluminum and the like) in a suitable organic solvent (benzene, an aliphatic hydrocarbon or the like) is allowed to contact with water to produce aluminoxane. Further, there is exemplified a method in which Ia trialkylaluminum (for example, trimethylaluminum and the like) is allowed to contact with a metal salt containing crystal water (for example, copper sulfate hydrate and the like) to produce aluminoxane.

The molar ratio of metal complex (1):scavenger b) employed preferably ranges from 0.1:1000 to 0.1:10, more preferably ranges from 0.1:1000 to 0.1:300, and most preferably from 0.14:600 to 0.14:400.

The catalyst system may contain the metal complex of the present invention as such or as in supported form on a supporting material.

A supporting material is defined as an inorganic or organic compound that does not dissolve in the inert hydrocarbon solvent in which the process of the invention is carried out. Suitable inorganic supports include silica, magnesium halides, such as $MgF_2$, $MgCl_2$, $MgBr_2$, $MgI_2$, zeolites, and alumina. Suitable organic supports include polymers. Some non-limiting examples of polymeric supports are polyolefins such as polystryrene, polypropylene and polyethylene, polycondensates such as polyamides and polyesters and combinations thereof.

The invention also relates to a supported catalyst which comprises a metal complex of the formula (1) on a supporting material and optionally a scavenger and/or activator. Preferred supporting material are mentioned above.

Polymerization

The invention further provides a process for the polymerization of a polymer by polymerizing at least one olefinic monomer comprising contacting said monomer with a metal complex of formula (1).

The preferred process for polymerization is generally concluded by consulting at least one olefinic monomer with the metal complex of the formula (1) or the catalyst system according to the present invention in the gas phase, in slurry, or in solution in an inert solvent preferable a hydrocarbon solvent. Suitable solvents are in the gas phase, in slurry, or in solution in an inert solvent preferably a hydrocarbon solvent. Suitable solvents are a $C_{5-12}$ hydrocarbon such as pentane, hexane, heptane, octane, isomers and mixtures thereof, cyclohexane, methylcyclohexane, pentamethyl heptane and hydrogenated naphta. The process of the invention may be conducted at temperatures from 10 to 250° C., depending on the product being made.

An olefinic monomer is understood to be a molecule containing at least one polymerizable double bond.

Suitable olefinic monomers are $C_{2-20}$ define. Preferred monomers include ethylene and $C_{3-12}$ alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, and $C_{4-12}$ straight chained or cyclic hydrocarbyl radicals which are unsubstituted or substituted by a $C_{1-4}$ alkyl radical. Illustrative non-limiting examples of such a-olefins are propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-hepta-decene, 1-octadecene, 1 nonadecene, 1-eicosene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 9-methyl-1-decene, 11-methyl-1-dodecene and 12-ethyl-1-tetradecene. These a-olefins may be used in combination.

The monomer may also be a polyene comprising at least two double bonds. The double bonds may be conjugated or non-conjugated in chains, ring systems or combinations thereof, and they may be endocyclic and/or exocyclic and may have different amounts and types of substituents. This means that the polyene may comprise at least one aliphatic, alicyclic or aromatic group, or combinations thereof.

Suitable polyenes include aliphatic polyenes and alicyclic polyenes. More specifically, aliphatic polyenes can be mentioned, such as 1,4-hexadiene, 3-methyl-1,4-hexadiene, 4-methyl-1,4-hexadiene, 5-methyl-1,4-hexadiene, 4-ethyl-1,4-hexadiene, 1,5-hexadiene, 3-methyl-1,5-hexadiene, 3,3-dimethyl-1,4-hexadiene, 5-methyl-1,4-heptadiene, 5-ethyl-1,4-heptadiene, 5-methyl-1,5-heptadiene, 6-methyl-1,5-heptadiene, 5-ethyl-1,5-heptadiene, 1,6-heptadiene, 1,6-octadiene, 4-methyl-1,4-octadiene, 5-methyl-1,4-octadiene, 4-ethyl-1,4-octadiene, 5-ethyl-1,4-octadiene, 5-methyl-1,5-octadiene, 8-methyl-1,5-octadiene, 5-ethyl-1,5-octadiene, 6-ethyl-1,5-octadiene, 1,6-octadiene, 6-methyl-1,8-octadiene, 7 methyl-1,6-octadiene, 6-ethyl-1,8-octadiene, 6-propyl-1,6-octadiene, 8-butyl-1,6-octadiene, 1,7-octadiene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 8-methyl-1,5-nonadiene, 5-ethyl-1,5-nonadiene, 6-ethyl-1,5-nonadiene, 6-methyl-1,6-nonadiene, 7-methyl-1,8-nonadiene, 8-ethyl-1,8-nonadiene, 7-ethyl-1,6-nonadiene, 7-methyl-1,7-nonadiene, 8-methyl-1,7-nonadiene, 7-ethyl-1,7-nonadiene, 1,8-nonadiene, 5-methyl-1,4-decadiene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-decadiene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-decadiene, 9-methyl-1,8-decadiene, 8-ethyl-1,8-decadiene, 1,9-decadiene, 1,5,9-decatriene, 6-methyl-1,6-undecadiene, 9-methyl-1,8-undecadiene and 1,13-tetradecadiene, 1,3-butadiene, isoprene.

Alicyclic polyenes may consist of at least one cyclic fragment. Examples of these alicyclic polyenes are vinylcyclohexene, vinylnorbornene, ethylidene norbornene, dicyclopentadiene, cyclooctadiene, 2,5-norbornadiene, 1,4-divinylcyclohexane, 1,3-divinylcyclohexane, 1,3-divinylcyclopentane, 1,5-divinylcyclooctane, 1-allyl-4-vinylcyclohexane, 1,4-diallylcyclohexane, 1-allyl-5-vinylcycloocatane, 1,5-diallylcyclooctane, 1-allyl-4-isopropenylcyclohexane, 1-isopropenyl-4-vinylcyclohexane and 1-isopropenyl-3-vinylcyclopentane, and 1,4-cyclohexadiene. Preferred polyenes are polyenes having at least one endocyclic double bond and optionally at least one exocyclic double bond, such as 5-methylene-2-norbornene and 5-ethylidene-2-norbornene, 5-vinylnorbornene, and 2,5-norbornadiene, dicyclopentadiene (DCPD) and vinylcyclohexene.

Examples of aromatic polyenes are divinylbenzene (including its isomers), trivinyl-benzene (including its isomers) and vinylisopropenylbenzene (including its isomers).

All of the above-mentioned monomers may be further substituted with at least one group comprising a heteroatom of group 13-17, or combinations thereof.

Homopolymers, copolymers on the basis of 2 or more of the above-mentioned olefinic monomers and also blends thereof can be prepared with the process of the present invention.

In a preferred embodiment copolymers on the basis of ethylene, at least one $C_{3-12}$ alpha olefin, preferably propylene and at least one non-conjugated diene, preferably a diene selected from the group consisting of 5-methylene-2-norbornene 5-ethylidene-2-norbornene, 5-vinylnorbornene, 2,5-norbornadiene, dicyclopentadiene and vinylcyclohexene, preferably from the group consisting of 5-ethylidene-2-norbornene and 5-vinylnorbornene are made with metal complex of the present invention.

The invention further relates to polymers obtainable with the metal complex of the present invention or the catalyst system of the present invention. Below, the invention will be elucidated on the basis of the following examples and comparative experiments, without being limited thereto.

EXAMPLES

Test Methods.
  Size Exclusion Chromatography (SEC) coupled to Refractive Index (RI) and Differential Viscometry (DV) detection. (SEC-DV)
Equipment: PL220 (Polymer Laboratories) SEC with PL220
  DRI concentration detector and
  Viscotek 220R viscometry detector.
  Detectors are operated in parallel configuration
  Degasser: PL-DG 802
Data processing: Viscotek data processing software, TriSEC
  2.7 or higher
  version
Columns: PLgel Olexis (4×)
Calibration: Universal calibration with linear polyethylene (PE) standard (molecular weight 0.4-4000 kg/mol)
Temperature: 160° C.
Flow: 1.0 ml/min
Injection volume; 0,300 ml
Solvent/eluent: Distilled 1,2,4-trichlorobenzene with about 1 g/l of Ionol stabilizer
Sample preparation: Dissolving for 4 hours at approx. 150
  Filtration through 1.2 micron Ag filter
  Sample concentration approx. 1.0 mg/ml Intrinsic Viscosity (IV) was measured at 135° C. decahydronaphthalen as solvent.

NMR ($^1$H, 300 MHz, $^{13}$C 75.4 MHz) spectra were measured on a Varian Mercury-VX 300 spectrometer.

Fourier transformation infrared spectroscopy (FT-IR), was used to determine the composition of the copolymers according to the method that is known in the art. The FT-IR measurement gives the composition of the various monomers in weight per cents relative to the total composition.

Synthesis of Compounds

General.

All manipulations were carried out using standard Schlenk line or dry-box techniques under an atmosphere of argon or dinitrogen. Solvents were degassed by sparging with dinitrogen and dried by passing through a column of the appropriate drying agent. Toluene was refluxed over sodium and distilled. Deutereted solvents were dried over potassium ($C_6D_6$) or $P_2O_5$ ($CDCl_3$ and $CD_2Cl_2$), distilled under reduced pressure and stored under dinitrogen in Teflon valve ampoules. NMR samples were prepared under dinitrogen in 5 mm Wilmad 507-PP tubes fitted with J. Young Teflon valves. $^1$H and $^{13}$C-{$^3$H} spectra were recorded on a Varian Mercury-VX 300 spectrometer at ambient temperature unless stated otherwise and referenced internally to residual protio-solvent ($^1$H) or solvent ($^{13}$C) resonances, and are reported relative to tetramethylsilane (d=0 ppm). Assignments were confirmed using two dimensional $^1$H—$^1$H and $^{13}$C—$^1$H NMR correlation experiments. Chemical shifts are quoted in δ (ppm) and coupling constants in Hz. Mass spectra were recorded by the mass spectrometry service of the University of Oxford. IR spectra were recorded on Nicolet Magna 560 E.S.P. FTIR, Perkin-Elmer 1710 or (for air-stable, solid samples) Broker Tensor 27 FT-IR (thin film deposition on diamond ATR module) spectrometers. Air-sensitive samples were prepared in a dry-box as Nujol mulls between NaCl plates, and the data are quoted in wavenumbers (cm$^{-1}$) within the range 4000-400 cm$^{-1}$.

FIGURES

FIG. 1 shows the X-ray structure of compound 3 of example 1

FIG. 2 shows the X-ray structure of compound 2 of example 2

SYNTHESIS OF COMPOUNDS FOR THE COMPARATIVE EXAMPLES

Cp*Ti{NC(Ph)N$^i$Pr$_2$}(η-1,4-C$_4$H$_4$Me$_2$) (Compound A) was prepared as described for compound 3 in WO2011076772 and WO2011076775.

Synthesis of Cp*Ti{NC(Ph)($^i$Pr$_2$N)}Me$_2$ (Compound B)

To a stirring toluene (15 mL) solution of Cp*Ti{NC(Ph)N$^i$Pr$_2$}Cl$_2$ (3) (1.00 g, 2.20 mmol) was added dropwise MeLi (2.80 mL, 1.6 M in Et$_2$O, 4.40 mmol) and the resulting solution was stirred for 16 h. The volatiles were then removed in vacuo and the yellow solid was then extracted into n-hexanes (50 mL). Concentration of the solution to ca 15 mL and subsequent storage at −30° C. for 24 h resulted in crystallisation of the desired product as large yellow crystals which were isolated and dried in vacuo. Yield=0.37 g (40%). The product was characterized by $^1$H-NMR and $^{13}$C-NMR.

Synthesis of Compounds for the Examples of the Invention

Synthesis of Cp*Ti{NC(Ph)N$^i$Pr$_2$}{η$^3$-CH$_2$C(Me)C(Me)CH$_2$BAr$^F_3$} (Compound 1)

To a solution of Cp*Ti{NC(Ph)N$^i$Pr$_2$}(η-2,3-C$_4$H$_4$Me$_2$) (0.30 g, 0.64 mmol) in toluene (20 mL) was added BAr$^F_3$ (0.33 g, 0.64 mmol) in toluene (20 mL). After ca. 30 s the solution changed to a darker colour. It was stirred for a further 2 h and the volatiles were removed in vacuo. The resulting green solid was washed with pentane (3×15 mL) and dried in vacuo. Yield=0.51 g (81%). The product was characterized by 1H-NMR and $^{13}$C-NMR.

Synthesis of Cp*Ti{NC(Ph)N$^i$Pr$_2$}{η$^3$-Et(CH)$_3$CH$_2$BAr$^F_3$} (Compound 2)

To a solution of Cp*Ti{NC(Ph)N$^i$Pr$_2$}(η-1,4-C$_4$H$_4$Me$_2$) (Compound A) (0.30 g, 0.64 mmol) in toluene (20 mL) was added BAr$^F_3$ (0.33 g, 0.64 mmol) in toluene (20 mL). After ca. 30 seconds the solution changed to a darker green colour. It was stirred for a further 2 h and the solvent was removed in vacuo. The resulting green solid was washed with pentane (3×15 mL), dried in vacuo. Yield=0.58 g (93%). The product was characterized by $^1$H—HNR and $^{13}$C—NMR.

Example 1

Synthesis of Cp*Ti{NC(Ph)N$^i$Pr$_2$}{η$^3$-CH$_2$C(Me)C(Me)CH$_2$BAr$^F_3$}($^t$BuNC) (Compound 3)

To a solution of Cp*Ti{NC(Ph)N$^i$Pr$_2$}{η$^3$-CH$_2$C(Me)C(Me)CH$_2$BAr$^F_3$} (Compound 1) (0.50 g, 0.51 mmol) in toluene (15 mL) was added t-BuNC (57.7 µL, 0.51 mmol). The solution immediately turned from green to dark red. After addition of n-hexanes (5 mL) the solution was left to stand for 16 h resulting in crystallisation of a red solid which was isolated, washed with n-hexanes (3×10 mL) and dried in vacuo. Yield=0.39 g (72%). Single crystals suitable for X-ray diffraction were grown from a toluene/n-hexanes solution at RT. Compound 3 can be stored in air for days without undergoing noticeable decomposition. The compound exists as a mixture of diastereomers in solution at 243 K: 3A and 3B in a ratio 60:40.

Common data: $^{19}$F NMR (Toluene-d$_8$, 282.2 MHz, 293 K): −130.1 (br m, o-F, 6F), −164.2 (br m, p-F, 3F), −167.4 (br m, m-F, 8F) ppm. $^{11}$B NMR (Toluene-d$_6$, 96.2 MHz, 293 K): −13.4 ppm. IR (NaCl plates, Nujol mull, cm$^{-1}$): 2171 (a, u(C≡N)), 1640 (w), 1617 (w), 1510 (m), 1419 (s), 1153 (s), 1075 (s), 1033 (w), 971 (s), 888 (m), 843 (m), 789 (w). Anal. found (calcd. for C$_{52}$H$_{53}$BF$_{15}$N$_3$Ti): C, 58.54 (58.72); H, 4.92 (5.02); N, 3.65 (3.95) %. EI-MS: m/z=512 (100%, [B(C$_6$F$_5$)$_3$]$^+$), 203 (100%, [NC(Ph)N$^i$Pr$_2$]$^+$), 100 (100%, [N$^i$Pr$_2$]$^+$).

Data for 3A: $^1$H NMR (CD$_2$Cl$_2$, 299.9 MHz, 243 K): 7.42-6.88 (5H, series of overlapping m, C$_6$H$_5$), 4.68 (1H, sept, CHMe$_2$ cis to C$_6$H$_5$, $^3$J=6.9 Hz), 3.46 (1H, br m, CHMe$_2$ trans to C$_6$H$_5$), 2.36 (1H, app d, CH$_2$BAr$^F_3$, $^2$J=9.8 Hz), 2.05 (3H, s, CH$_2$C(Me)C(Me)CH$_2$BAr$^F_3$), 1.91 (1H, d, CH$_2$C(Me)C(Me)CH$_2$BAr$^F_3$, $^2$J=7.2 Hz), 1.71 (9H, s, $^t$BuNC), 1.55 (15H, s, C$_5$Me$_5$), 1.48 (3H, s, CH$_2$C(Me)C(Me)CH$_2$BAr$^F_2$), 1.20 (3H, d, CHMe$_2$, trans to C$_6$H$_5$, $^3$J=6.5 Hz), 1.12 (3H, d, CHMe$_2$ trans to C$_6$H$_5$, $^3$J=6.5 Hz), 1.02 (3H, d, CHMe$_2$ cis to C$_6$H$_5$, $^3$J=6.9 Hz), 0.91 (3H, d, CHMe$_2$ cis to C$_6$H$_5$, $^3$J=6.9 Hz), 0.87 (1H, CH$_2$C(Me)C(Me)CH$_2$BAr$^F_3$ (overlapping with CHMe$_2$ of 3B)), −0.27 (1H, app d, $^2J$=9.8 Hz, CH$_2$BAr$^F_3$) ppm. 13C-{$^1$H} NMR (CD$_2$Cl$_2$, 75.4 MHz, 293 K): 160.9 (NC(Ph)N$^i$Pr$_2$), 147.8 (C$_6$F$_5$), 147.4 ($^t$BuNC), 139.5 (CH$_2$C(Me)C(Me)CH$_2$BAr$^F_3$), 138.7 (C$_6$F$_5$), 136.2 (i-C$_6$H$_5$), 135.5 (C$_6$F$_5$), 129.1 (o or m-C$_6$H$_5$), 128.3 (m- or o-C$_6$H$_6$), 126.4 (p-C$_6$H$_5$), 123.9 (CH$_2$C(Me)C(Me)CH$_2$BAr$^F_3$), 118.9 (C$_5$Me$_5$), 74.3 (CH$_2$C(Me)C(Me)CH$_2$BAr$^F_3$), 58.6 (CMe$_3$), 53.3 (CHMe$_2$ trans to C$_6$H$_5$), 47.0 (CHMe$_2$ cis to C$_6$H$_5$), 30.3 (CMe$_3$), 25.5 (CH$_2$C(Me)C(Me)CH$_2$BAr$^F_3$), 22.3 (CH$_2$C(Me)C(Me)CH$_2$BAr$^F_3$), 21.7 (CHMe$_2$, trans to C$_6$H$_5$), 21.5 (CHMe$_2$ trans to C$_6$H$_6$), 21.4 (CHMe$_2$, cis to C$_6$H$_6$), 19.9 (CHMe$_2$ cis to C$_5$H$_5$), 11.9 (C$_5$Me$_5$) ppm (CH$_2$BAr$^F_3$ and i-C$_6$F$_5$ were not observed).

Data for 3B: $^1$H NMR (CD$_2$Cl$_2$, 299.9 MHz, 243 K): 7.42-6.88 (5H, series of overlapping m, C$_6$H$_5$), 3.39 (2H, sept, CHMe$_2$, $^3J$=7.1 Hz), 2.17 (1H, d, CH$_2$C(Me)—C(Me)CH$_2$BAr$^F_3$, $^2J$ 5.5 Hz), 2.01 (1H, app d, CH$_2$BAr$^F_3$, $^2J$=11.7 Hz), 1.86 (3H, s, CH$_2$C(Me)C(Me)CH$_2$BAr$^F_3$), 1.83 (15H, a C$_5$Me$_5$), 1.68 (3H, s, CH$_2$C(Me)C(Me)CH$_2$BAr$^F_3$), 1.30 (9H, s, $^t$BuNC), 1.23 (1H, CH$_2$C(Me)—C(Me)CH$_2$BAr$^F_3$ (overlapping with CHMe$_2$ of 3A)), 0.85 (6H, d, CHMe$_2$, $^3J$=7.5 Hz), 0.81 (6H, d, CHMe$_2$, $^3J$=6.6 Hz), −0.38 (1H, app d, $^2J$=11.7 Hz, CH$_2$BAr$^F_3$) ppm. $^{13}$C-{$^1$H} NMR (CD$_2$Cl$_2$, 75.4 MHz, 293 K): 164.0 (NC(Ph)N$^i$Pr$_2$), 147.2 ($^t$BuNC), 138.9 (CH$_2$C(Me)C(Me)CH$_2$BAr$^F_3$), 136.3 (i-C$_6$H$_5$), 129.2 (o- or m-C$_6$H$_6$), 129.0 (o- or m-C$_6$H$_5$), 127.9 (CH$_2$C(Me)C(Me)CH$_2$BAr$^F_3$), 125.4 (p-C$_6$H$_5$), 118.4 (C$_5$Me$_5$), 70.8 (CH$_2$C(Me)C(Me)CH$_2$BAr$^F_3$), 57.8 (CMe$_3$), 46.9 (CHMe$_2$), 29.6 (CMe$_3$), 24.6 (CH$_2$C(Me)C(Me)CH$_2$BAr$^F_2$), 24.0 (CHMe$_2$), 22.2 (CH$_2$C(Me)C(Me)CH$_2$BAr$^F_3$), 12.3 (C$_5$Me$_5$) ppm (CH$_2$BAr$^F_3$ and i-C$_6$F$_5$ were not observed; other C$_6$F$_5$ resonances could not be distinguished from those of 3A)

Example 2

Synthesis of Cp*Ti{NC(Ph)N$^i$Pr$_2$}{η$^3$-Et(CH)$_3$CH$_2$BAr$^F_3$}($^t$BuNC) (Compound 4)

To a solution of Cp*Ti{NC(Ph)N$^i$Pr$_2$}{η$^3$-Et(CH)$_3$CH$_2$BAr$^F_3$} (Compound 2) (0.50 g, 0.51 mmol) in toluene (15 mL) was added $^t$BuNC (57.7 μL, 0.51 mmol). The solution immediately turned from green to dark red and on standing at RT for 3 h, dark red crystals of Compound 4 had grown. These were isolated, washed with n-hexanes (3×10 mL), and dried in vacuo. Yield=0.42 g (77%). Compound 4 can be stored in air for days without undergoing noticeable decomposition. $^1$H NMR (CD$_2$Cl$_2$, 499.9 MHz, 293 K): 7.35-6.97 (5H, series of m, C$_6$H$_5$), 4.44 (1H, dd, EtCHCH, $^3J$=13.9 Hz, 15.8 Hz), 3.53 (2H, br m, CHMe$_2$), 3.08 (1H, app d, CH$_2$BAr$^F_3$, $^2J$=10.3 Hz), 2.39 (1H, m, CHCH$_2$BAr$^F_3$), 1.91 (1H, app d, CH$_2$BAr$^F_3$, $^2J$=10.3 Hz), 1.78 (1H, m, CHEt), 1.69 (15H, s, C$_5$Me$_5$), 1.60 (9H, s, $^t$BuNC), 1.46 (2H, br m, CH$_2$Me), 1.27 (6H, br d, CHMe$_2$), 0.97 (6H, d, CHMe$_2$, $^3J$ 7.8 Hz), 0.81 (3H, t, CH$_2$Me, $^3J$=8.2 Hz) ppm. $^{13}$C-{$^1$H} NMR (CD$_2$Cl$_2$, 125.8 MHz, 293 K): 164.0 (NC(Ph)N$^i$Pr$_2$), 148.8 (C$_6$F$_5$), 138.9 ($^t$BuNC), 138.7 (C$_6$F$_5$), 138.6 (i-C$_6$H$_5$), 136.9 (C$_6$F$_5$), 129.6 (o- or m-C$_6$H$_5$), 129.1 (m- or o-C$_6$H$_5$), 128.8 (p-C$_5$H$_5$), 125.8 (CHCH$_2$BAr$^F_2$), 124.8 (EtCHCH), 118.9 (C$_5$Me$_5$), 92.2 (CHEt), 58.9 (CMe$_3$), 48.1 (CHMe$_2$), 33.0 (CH$_2$BAr$^F_3$), 31.5 (CH$_2$Me), 30.5 (CMe$_3$), 21.7 (CHMe$_2$), 21.3 (CHMe$_2$), 19.1 (diene CH$_2$Me), 12.0 (C$_5$Me$_5$) ppm (i-C$_6$F$_5$ was not observed). $^{19}$F NMR (Toluene-d$_8$, 282.2 MHz, 293 K): ~131.3 (m, o-F, 6F), −162.8 (m, p-F, 3F), −166.3 (m, m-F, 6F) ppm. $^{11}$B NMR (Toluene-d$_6$, 96.2 MHz, 293 K): −12.3 ppm. IR (NaCl plates, Nujol mull, cm$^{-1}$): 2177 (s, u(C≡N)), 1509 (s), 1331 (s), 1269 (s), 1194 (m), 1158 (m), 1136 (m), 1076 (s), 1026 (w), 918 (m), 885 (w), 789 (w), 758 (w), 726 (s), 571 (m). Anal. found (calcd. for C$_{52}$H$_{53}$BF$_{15}$N$_3$Ti): C, 58.56 (58.72); H, 5.16 (5.02); N, 3.73 (3.95) %. EI-MS: m/z=512 (100%, [B(C$_6$F$_5$)$_3$]$^+$), 494 (10%, [M-B(C$_6$F$_5$)$_3$-$^t$Bu]$^+$), 83 (80%, [$^t$BuNC]$^+$), 57 (100%, [N$^i$Pr]$^+$). Single crystals suitable for X-ray diffraction were grown from a toluene/n-hexanes solution at room temperature.

Polymerization Example

Batch EPDM Copolymerisation (General Process)

The batch copolymerizations were carried out in a 2-liter batch autoclave equipped with a double intermig and baffles. The reaction temperature was set on 90° C. and controlled by a Lauda Thermostat. The feed streams (solvents and monomers) were purified by contacting with various adsorption media to remove catalyst killing impurities such as water, oxygen and polar compounds as is known to those skilled in the art. During polymerisation the ethylene and propylene monomers were continuously fed to the gas cap of the reactor. The pressure of the reactor was kept constant by a back pressure valve.

In an inert atmosphere of nitrogen, the reactor was filled with pentamethyl heptanes (PMH) (950 mL), Isobutylaluminoxane (IBAO-65, 13 wt %, hexane solutions; Akzo Nobel, 3.5 wt % Al in n-hexanes), BHT, 5-ethylidene-2-norbornene (ENB) (0.7 mL) and 5-vinyl-2-norbornene (VNB) (0.7 mL). The reactor was heated to 90° C., while stirring at 1350 rpm. The reactor was pressurized and conditioned under a determined ratio of ethylene, propylene and hydrogen (0.35 NL/h) After 15 minutes, the catalyst components were dosed under inert conditions as toluene or n-hexanes solutions into the reactor and the catalyst vessel was rinsed with PMH (50 mL) subsequently. (When B(C$_6$F$_5$)$_3$ was used; the borane was added directly after the catalyst was added. This was activation via abstraction of the $^t$BuNC ligand in the case of Compound 4 and activation via abstraction of the methyl and diene ligands in the cases of Compounds B and D). After 10 minutes of polymerisation, the monomer flow was stopped and the solution was carefully dumped in an Erlenmeyer flask of 2 L, containing a solution of Irganox-1076 in isopropanol and dried over night at 100° C. under reduced pressure. The polymers were analysed for molecular weight distribution (SEC-DV) and composition (FT-IR).

The experimental conditions and results are given in table 1.

TABLE 1

| Example | Organo-metallic Compound | IBAO (μmol) | Metal-organic compound dosage (μmol) | Equivs of Added B(C$_6$F$_5$)$_3$ Cocal. | Yield (g) | Residual Ti in polymer (ppm)[1] | Incorporated C2 (wt %) | ENB (wt %) | VNB (wt %) | Mw (kg/mol) | Mw/Mn |
|---|---|---|---|---|---|---|---|---|---|---|---|
| 1 | 4 | 450 | 0.14 | 0 | 5.31 | 1.26 | 54.0 | 1.03 | 0.72 | 125 | 2.1 |
| 2 | 4 | 450 | 0.14 | 1 | 8.85 | 0.76 | 48.9 | 0.99 | 0.67 | — | — |
| 5 | A | 450 | 0.14 | 0 | 0.88 | 7.62 | — | — | — | — | — |
| 6 | A | 450 | 0.14 | 1 | 8.0 | 0.84 | 53.0 | 1.09 | 0.75 | 120 | 2.4 |

TABLE 1-continued

| Example | Organo-metallic Compound | IBAO (μmol) | Metal-organic compound dosage (μmol) | Equivs of Added B(C$_5$F$_5$)$_3$ Cocal. | Yield (g) | Residual Ti in polymer (ppm)[1] | Incorporated C2 (wt %) | ENB (wt %) | VNB (wt %) | Mw (kg/mol) | Mw/Mn |
|---|---|---|---|---|---|---|---|---|---|---|---|
| 9 | B | 450 | 0.14 | 0 | 3.10 | 2.16 | — | — | — | — | — |
| 10 | B | 450 | 0.14 | 1 | 7.49 | 0.89 | 53.4 | 0.96 | 0.66 | 100 | 2.6 |

[BHT]/[Al] = 2 mol/mol;
C3 feed = 400 NL/h;
C2 feed = 200 NL/h;
ENB feed = 0.7 ml;
VNB feed = 0.7 ml;
H2 feed = 0.35 NL/h
T = 90° C.;
P = 7 barg
[1]Calculated value

What is claimed is:

1. A metal complex of the formula (1)

$$CyAMX(L)_n \qquad (1)$$

wherein:
Cy is a cyclopentadienyl-type ligand;
M is a metal of group 4;
A is an amidine-containing ligand moiety, represented by formula 2:

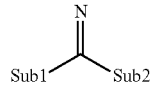

(2)

wherein the amidine-containing ligand is covalently bonded to the metal M via the imine nitrogen atom, and Sub1 is a substituent comprising a group 14 atom through which Sub1 is bonded to the imine carbon atom and Sub2 is a substituent comprising a heteroatom of group 15, through which Sub2 is bonded to the imine carbon atom;
X is an allyl borate ligand derived from a conjugated diene ligand and a borane; and
L is a neutral Lewis basic ligand and "n" is 1 to an amount that specifies the 18-electron rule.

2. The metal complex according to claim 1, wherein L is an ether, a thioether, an amine, a tertiary phosphane, an imine, a nitrile, are isonitrile, or a bi- or oligodentate donor.

3. The metal complex according to claim 1 wherein L is t-butylisonitrile.

4. The metal complex according to claim 1 wherein M is titanium.

5. The metal complex according to claim 1 wherein n is 1 or 2.

6. The metal complex according to claim 1, wherein X is an allyl borate ligand derived from a diene with a borane of the general formula $BQ_1Q_2Q_3$ wherein $Q_1$, $Q_2$, and $Q_3$ are individually a halogen atom, hydrocarbon group, halogenated hydrocarbon group, substituted silyl group, alkoxy group or di-substituted amino group.

7. The metal complex according to claim 1, wherein Sub1 is a phenyl or substituted phenyl residue and Sub2 is an amino radical of the formula $-NR^4R^5$ with $R^4$ and $R^5$ being individually selected from the group of aliphatic hydrocarbyl, halogenated aliphatic hydrocarbyl, aromatic hydrocarbyl, and halogenated aromatic hydrocarbonyl residues, one of $R^4$ and $R^5$ may optionally form a heterocyclic structure with the other of $R^4$ and $R^5$, or with Sub1.

8. Process for manufacturing the metal complex according to claim 1, the process comprising reacting a metal complex of the formula (3)

$$CyAMX \qquad (3)$$

with a Lewis base L.

9. The process according to claim 8, further comprising forming the metal complex of formula (3) by reacting a borane and a metal complex of formula (4)

$$CyAMD \qquad (4)$$

wherein D is a conjugated diene.

10. A catalyst system comprising:
a) the metal complex according to claim 1; and
b) a scavenger.

11. The catalyst system according to claim 10, wherein the scavenger b) is a hydrocarbyl of a metal or metalloid of any of groups 1-13 or its reaction products with at least one sterically hindered compound containing a group 15 or 16 atom.

12. A process for preparing a polymer, the process comprising contacting at least one olefinic monomer with the catalyst according to claim 1 to polymerize the monomers.

13. A process for preparing a polymer, the process comprising contacting at least one olefinic monomer with the catalyst system according to claim 10 to polymerize the monomers.

14. The process according to claim 12, wherein the at least one olefinic monomer comprises ethylene and at least a $C_3$-$C_{12}$-α-olefin.

15. The process according to claim 12, wherein the at least one olefinic monomer comprises ethylene, at least one $C_{3-12}$ alpha olefin, and at least one non-conjugated diene.

16. The process according to claim 15, wherein the at least one non-conjugated diene is a diene selected from the group consisting of 5-methylene-2-norbornene, 5-ethylidene-2-norbornene, 5-vinylnorbornene, 2,5-norbornadiene, dicyclopentadiene, and vinylcyclohexene.

17. The metal complex according to claim 1, wherein;
L is t-butylisonitrile;
M is titanium;
n is or 2;
X is an allyl borate ligand derived from a dims with a borane of the general formula $BQ_1Q_2Q_3$ wherein B is borane, and $Q_1$, $Q_2$, and $Q_3$ are individually a halogen atom, hydrocarbon group, halogenated hydrocarbon group, substituted silyl group, alkoxy group or di-substituted amino group, and they may be the same or different; and Sub1 is a phenyl or substituted phenyl residue and Sub2 is an amino radical of the formula —NR$^4$R$^5$ with R$^4$ and R$^5$ being individually selected from the group of aliphatic hydrocarbyl, halogenated aliphatic hydrocarbyl, aromatic hydrocarbyl, halogenated aromatic hydrocarbonyl residues, and one of R$^4$ or R$^5$ optionally forms a heterocyclic structure with the other of R$^4$ or R$^5$, or with Sub1.

18. The metal complex according to claim 1, wherein the borane is selected from the group consisting of tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluoro-phenyl)-borane, phenyl-bis(pentafluorophenyl)borane, and tris(pentafluoro-phenyl)-borane (B(C$_6$F$_5$)$_3$).

* * * * *